United States Patent [19]
Masuda et al.

[11] Patent Number: 6,158,864
[45] Date of Patent: *Dec. 12, 2000

[54] APPARATUS FOR PHOTOTAKING THE IMAGE OF AN EYE COMPRISING SYSTEMS FOR CONVERTING AN IMAGE SIGNAL FROM AN IMAGE PICKUP ELEMENT INTO ANIMATED-PICTURE-DISPLAY AND DIGITAL-IMAGE SIGNALS

[75] Inventors: Takashi Masuda, Yamato; Takeshi Kitamura, Utsunomiya; Kazuhiro Matsumoto, Yono; Motoya Takai, Kawasaki; Hiroshi Nishihara; Tetsuji Ogawa, both of Utsunomiya, all of Japan

[73] Assignee: Canon Kabushiki Kaisha, Tokyo, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/825,130

[22] Filed: Mar. 27, 1997

[30] Foreign Application Priority Data

Mar. 29, 1996 [JP] Japan ................................. 8-103162

[51] Int. Cl.$^7$ .............................................. A61B 3/14
[52] U.S. Cl. ................................. 351/206; 351/210
[58] Field of Search .............................. 351/205, 206, 351/210, 200

[56] References Cited

U.S. PATENT DOCUMENTS

| | | | |
|---|---|---|---|
| 4,541,010 | 9/1985 | Alston | 358/44 |
| 4,660,946 | 4/1987 | Nakamura et al. | 351/212 |
| 4,710,003 | 12/1987 | Masuda et al. | 351/212 |
| 4,848,896 | 7/1989 | Matsumoto | 351/211 |
| 4,952,049 | 8/1990 | Matsumoto | 351/211 |
| 5,056,522 | 10/1991 | Matsumura et al. | 128/645 |
| 5,302,979 | 4/1994 | Maeda et al. | 351/212 |
| 5,455,644 | 10/1995 | Yazawa et al. | 351/206 |
| 5,500,696 | 3/1996 | Masuda et al. | 351/205 |
| 5,530,494 | 6/1996 | Ogawa et al. | 351/206 |
| 5,614,967 | 3/1997 | Ishikawa et al. | 351/210 |

*Primary Examiner*—Huy Mai
*Attorney, Agent, or Firm*—Fitzpatrick, Cella, Harper & Scinto

[57] ABSTRACT

An apparatus for phototaking the image of an eye to be examined has an image pickup element for picking up the image of the eye to be examined, a first signal converting system for converting an image signal from the image pickup element into a signal for animated picture display, a second signal converting system for converting the image signal from the image pickup element into a digital image signal, and an image pickup element drive system for executing the drive systems of the image pickup element corresponding to the first and second signal converting systems.

10 Claims, 3 Drawing Sheets

APPARATUS FOR PHOTOTAKING THE IMAGE OF AN EYE COMPRISING SYSTEMS FOR CONVERTING AN IMAGE SIGNAL FROM AN IMAGE PICKUP ELEMENT INTO ANIMATED-PICTURE-DISPLAY AND DIGITAL-IMAGE SIGNALS

BACKGROUND OF THE INVENTION

1. Filed of the Invention

This invention relates to an ophthalmic phototaking apparatus for effecting the recording and display of the image of an eye to be examined.

2. Related Background Art

As an eye fundus camera, there is known a system in which the image of an eye to be examined is picked up by a continuously light emitting light source, such as a halogen lamp, and the alignment with the eye to be examined or the observation of a region to be phototaken is effected by the use of an optical finder or a television monitor and an examiner pushes a switch to make a strobe emit light to thereby record the image of the fundus of the eye on silver salt film.

Also, in recent years, recording media have been made electronic by the development of electronic image art and there have been widely used a system in which, as is conventional, observation is effected by an optical finder or a television camera for exclusive use and recording is effected with an examiner's switch being recognized, a light source made to emit light, and a television signal, which is outputted from the television camera exclusively for recording on an analog recording device, such as a magnetic tape or still video and the reproduced image thereof is displayed on a television monitor, and a system in which a television signal is A/D-converted and an image is stored in a memory device, such as a frame memory and is again D/A-converted into a television signal, which is then displayed on a television monitor.

Particularly, among systems characterized by a high quality image, there is one in which for phototaking, a digital output is possible from a high resolution image pickup element used exclusively for still pictures, and this system is designed such that observation is effected by a television camera for exclusive use or an optical finder and image recording is effected with a digital output from the camera transferred to a discrete personal computer through an interface such as SCSI or PCMCIA, and thereafter displayed by software for recording/image display.

However, in the above-described eye fundus camera wherein recording is effected on an electronic recording medium, two optical systems and two television cameras become necessary, such as an optical finder or a television camera for observation and a television camera for recording or an image pickup element exclusively for still pictures, and this leads to a high cost. Particularly, in an apparatus wherein as in non-mydriatic eye fundus phototaking, observation is effected by infrared light and color phototaking is effected by visible light, an infrared television camera for observation and a color camera for phototaking become necessary, and even if use is made of an expensive three-plate type color camera to make the most of the resolving power of a television signal for phototaking, a television signal band is limited in a generally used television signal and there is a limit to the resolving power obtained.

There is also an eye fundus camera using a digital camera containing therein an A/D converter in which the number of pixels of an image pickup element is great and which can provide a highly minute image, and this is exclusively used for still pictures in the relation of transfer time for data, and cannot display an animated picture at a frame rate required during observation. Accordingly, during observation, a television camera and an optical finder exclusively for observation become discretely necessary.

Also, to display the still pictures of these discretely from this, it is necessary to transfer data to a personal computer or a work station through an interface such as SCSI or PCMCIA contained in the camera, and display the data on a display for the computer by software for exclusive use, and to see the phototaken data, there is the problem that a large computer and a monitor must be installed near the apparatus.

SUMMARY OF THE INVENTION

It is a first object of the present invention to eliminate the above-noted problem and to provide an ophthalmic phototaking apparatus in which an image having the highest resolving power in both of observation and phototaking can be obtained by a single image pickup means.

It is a second object of the present invention to provide an ophthalmic phototaking apparatus which can display a highly minute image in the phototaking apparatus body.

It is a third object of the present invention to provide an ophthalmic phototaking apparatus which can simply effect the confirmation of a phototaken image, the alignment of an eye to be examined, and the selection of a region to be phototaken.

DESCRIPTION OF THE PREFERRED EMBODIMENT

Figure 1:
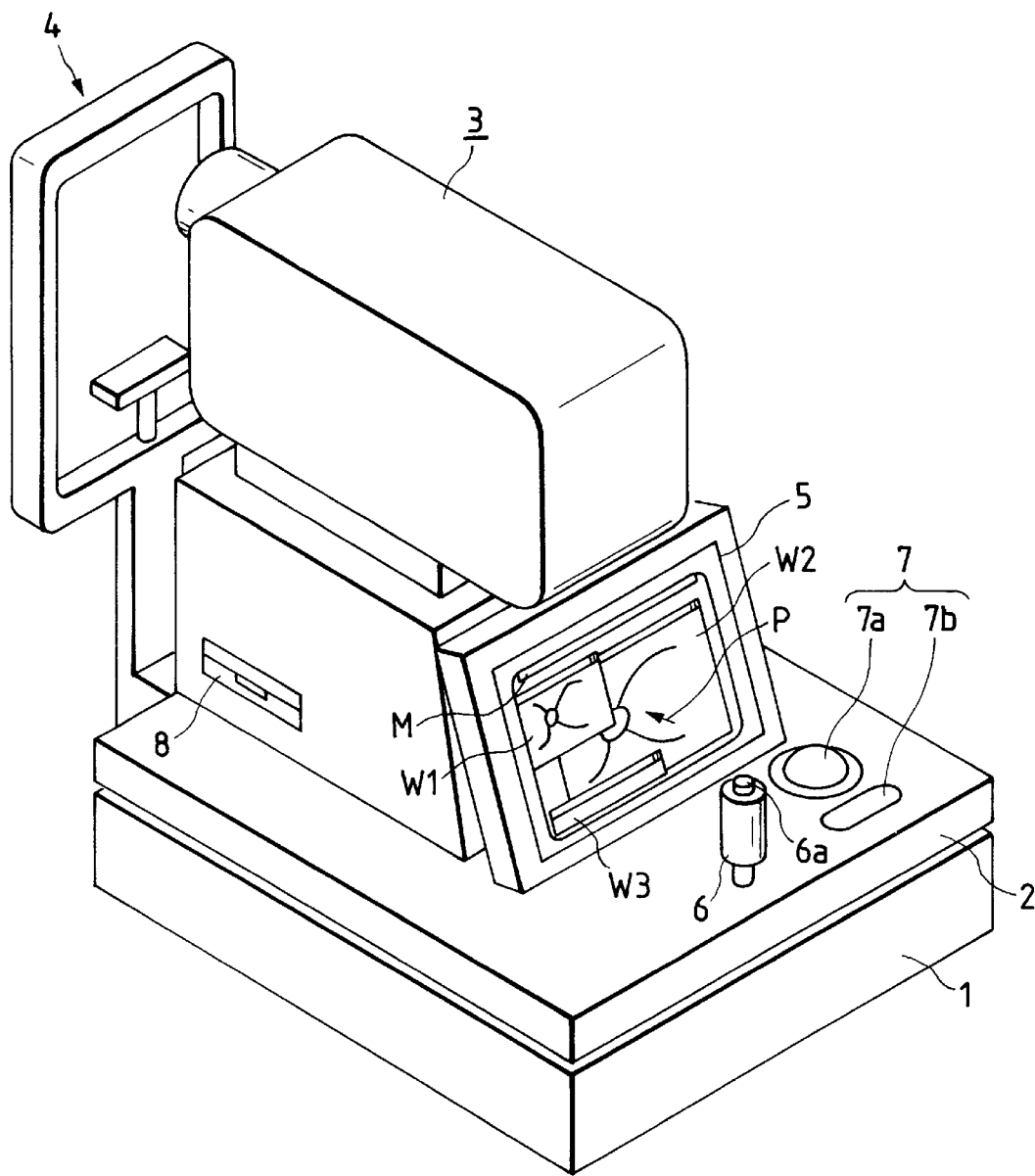
FIG. 1 is a perspective view of an embodiment of the present invention.

The invention will hereinafter be described in detail with respect to an embodiment thereof shown in the drawings.

Referring to FIG. 1 which is a perspective view of an eye fundus camera for eye fundus, a movable table 2 is placed on a fixed bed 1, a phototaking portion 3 is fixed on the movable table 2, and a face fixing member 4 is mounted on that side of the fixed bed 1 which is adjacent to an examinee. On that side of the movable table 2, which is adjacent to an examiner, there are disposed a liquid crystal display 5 for a computer such as SVGA, an operating rod 6 having a phototaking switch 6a, and a pointing device 7 comprising a track ball 7a and a setting button 7b, and besides an optical system and an electric circuit not shown in FIG. 1, image recording means 8 such as MO, CD-ROM or a hard disc is mounted on the phototaking portion 3.

In the liquid crystal display 5, there are displayed an animated picture image in a window W1, a phototaken still picture image in a window W2, and information such as a patient's name and ID in a window W3, and on a menu bar M, there are displayed operation menus, such as the inputting of patient information, the display and non-display and movement of each window and enlargement and reduction of the images, and a pointer P is moved and selected by the track ball 7a, and the setting button 7b can be depressed to effect setting.

Figure 2:
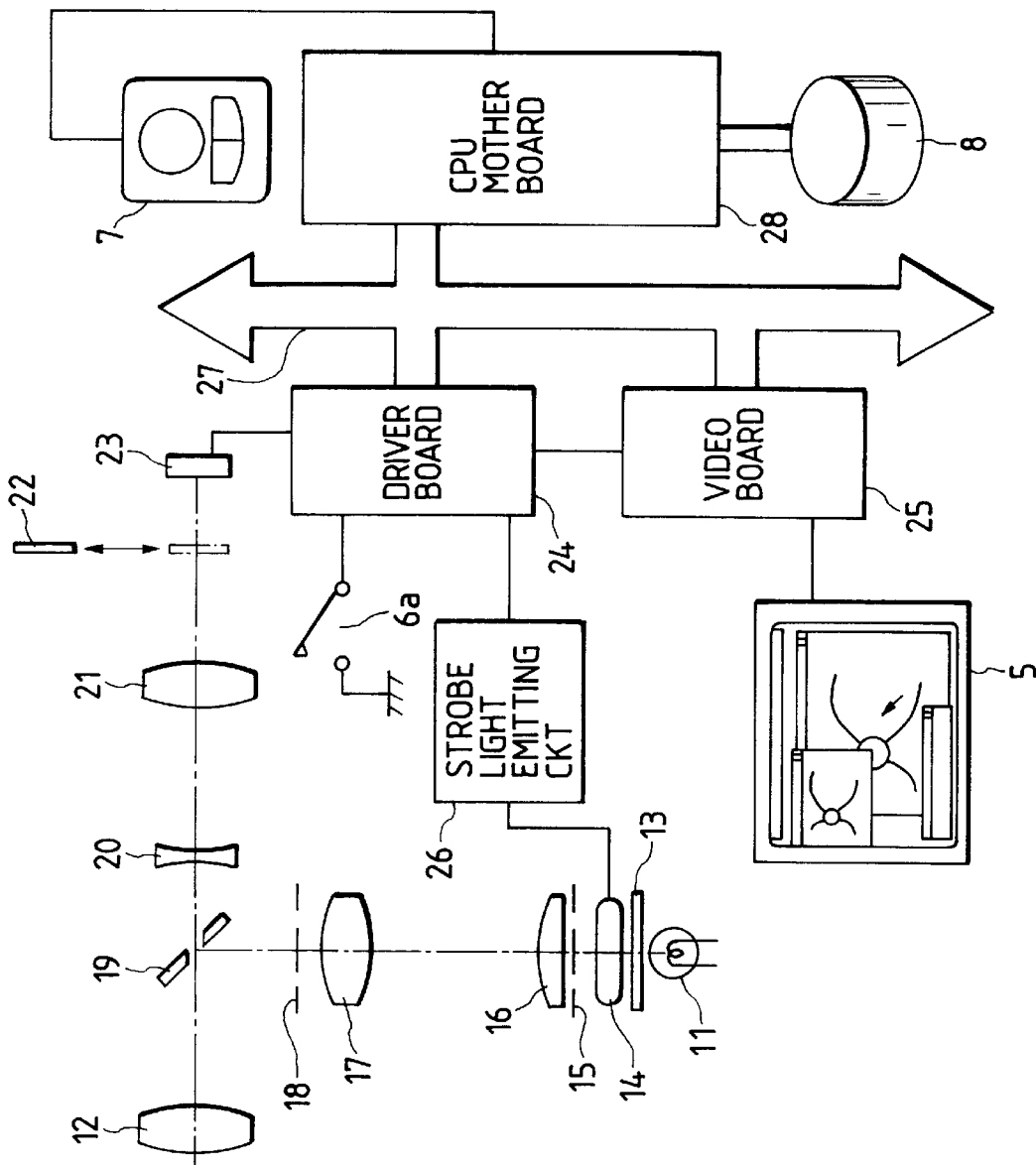
FIG. 2 shows the construction of an optical system and a block circuit.

FIG. 2 shows the construction of an optical system and an electric block circuit in the phototaking portion 3, and on an optical path leading from a light source 11 for observation continuously emitting light, like a halogen lamp, to an objective lens 12, there are successively arranged a visible light cut filter 13, a light source 14 for phototaking, such as a strobe, a ring slit 15, a field lens 16, a relay lens 17 for illumination, a baffle for eliminating scattered light in an eye, and an apertured mirror 19. On an optical path behind the apertured mirror 19, there are arranged a focusing lens 20, an image pickup lens 21, an infrared absorbing filter 22 removably insertable into the optical path, and an image pickup element 23 producing a color signal by a stripe filter or the like.

The output of the image pickup element 23 is connected to a driver board 24, a video board 25 for computer display control capable of displaying a television signal, a liquid crystal display 5 in succession, and the output of the driver board 24 is connected to the phototaking switch 6a and to the light source 14 for phototaking through a strobe light emitting circuit 26, and the input and output of the driver board 24 and video board 25 are connected to a universal bus 27 for a computer, such as a multibus or a PCI bus.

Besides a CPU, memory elements such as a ROM and a RAM and a CPU mother board 28 having an interface for controlling the universal bus 27 are connected to the universal bus 27. The image recording means 8 for recording image information and patient information such as the name and ID of a patient and the pointing device 7 are connected to the CPU mother board 28 through an interface such as SCSI or IDE and an interface such as RS-232C, respectively.

The CPU mother board 28 is designed to record the image of the fundus of an eye with the image information and the patient information such as the ID and to name of the patient on the image recording means 8, and move the pointer P display on the liquid crystal display 5 by the pointing device 7 to thereby perform operations such as the erasing, enlargement and reduction of the windows W1 to W3, the enlargement and reduction of the image, and the recording and retrieval of a still image onto the image recording means 8.

Figure 3:
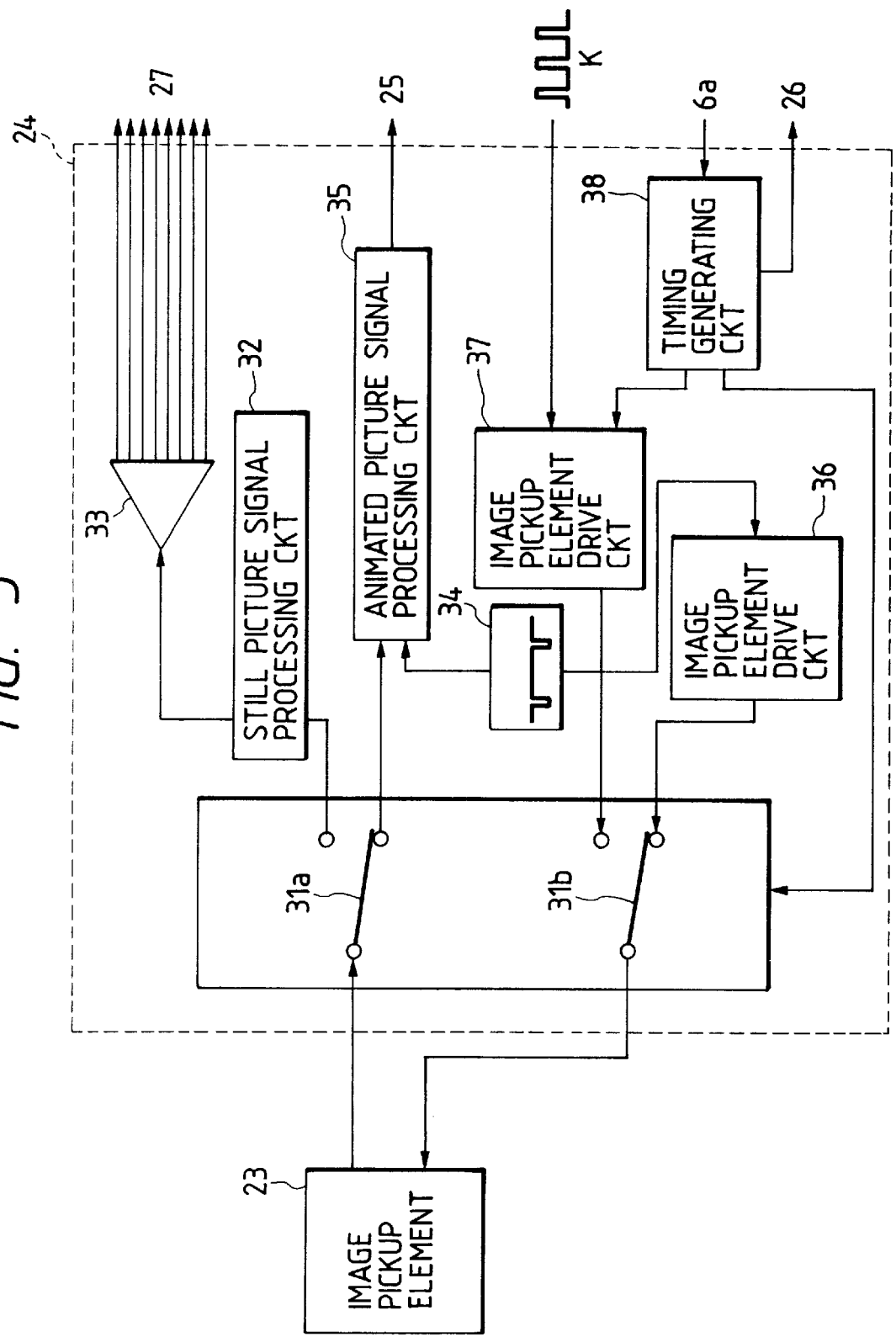
FIG. 3 shows the construction of the block circuit of a driver board.

Referring to FIG. 3 which shows the construction of the electric block circuit of the driver board 24, the input and output of the image pickup element 23 are connected to two switches 31a and 31b comprising multiplexers, and electromagnetic relays or the like in the driver board 24. Each of the switches 31a and 31b has its two contacts adapted to be changed over, and one contact of the switch 31a is connected to the external universal bus 27 through a still picture signal processing circuit 32 and a circuit 33 such as an A/D converter or a bus driver, and the other contact of the switch 31a, with the output from a synchronizing signal generator 34, is connected to the external video board 25 through an animated picture signal processing circuit 35.

Also, the output from the synchronizing signal generator 34 is connected to one contact of the switch 31b through an image pickup element drive circuit 36 for animated pictures, the output of an image pickup element drive circuit 37 for still pictures is connected to the other contact of the switch 31b, the output from an external clock K is connected to the image pickup element drive circuit 37 for still pictures, and further the output of the external phototaking switch 6a is connected to the image pickup element drive circuit for still pictures through a timing generating circuit 38, the output of which is connected to the external strobe light emitting circuit 26 and the switch 6a in the driver board 24.

A stripe filter usually used in a color camera has a wavelength selecting property for a visible light component, but has a characteristic of transmitting infrared light therethrough and therefore, by the infrared absorbing filter 22 being brought out of the optical path, the image pickup element 23 can be used as an image pickup element 23 having sensitivity to infrared light. In this case, a color filter differs in transmittance of infrared light depending on its color filtering characteristics and therefore, as a result, the image looks colored, but this can be corrected by the design of the driver board 24.

In the case of the present embodiment, if the television signal from the driver board 24 is once inputted to the video board 25 and by the use of the processing function of the video board 25, for example, the constant of the look-up table of each of R, G and B channels is preset in accordance with the output from the image pickup element 23, display can be effected on the liquid crystal display 5 with the color by the difference in the infrared-light-transmittance of the stripe filter erased. At present, the video board 25 having a television signal input terminal and displaying characters, graphics, images, etc. with a television animated image on a computer display at a high speed is recently widely used and therefore, if such a video board is used, it will be possible to construct the apparatus inexpensively.

With the above-described construction, an examiner moves the pointer P to the menu bar M on the liquid crystal display 5 by the track ball 7a disposed on the body to thereby select the inputting of the patient information, the display or nondisplay and movement of the windows W1, W2 and W3, and the enlarged or reduced display of the image, etc., and depresses the setting button 7b to thereby effect setting. Thereby, the image can be suitably recorded or the image preserved on the image recording means 8 can be displayed on the liquid crystal display 5.

When the light source 11 for observation is turned on, a light beam emitted from the light source 11 for observation has its visible light wavelength component cut by the visible light cut filter 13 and is transmitted through the light source 14 for phototaking, and illuminates the ring slit 15. Further, the light beam passes through the field lens 16, the relay lens 17 for illumination and the baffle 18, and is reflected by the marginal portion of the apertured mirror 19, and illuminates the fundus of the eye to be examined by the objective lens 12. The reflected light from the fundus of the eye passes through the objective lens 12 and the central aperture of the apertured mirror 19, and is imaged on the image pickup element 23 by the focusing lens 20 and the image pickup lens 21.

At this time, in the driver board 24, a predetermined television signal is generated from the synchronizing signal generator 34, and in accordance with the timing of this synchronizing signal, the image pickup element 23 is driven by the image pickup element drive circuit 36 for animated pictures, and in the driver board 24, the signal from the image pickup element 23 is inputted to the animated picture signal processing circuit 35 coupled thereto by the switch 31a, and is converted into a television signal for general use, such as NTSC composite, Y/C separation and RGB separation, and as a television signal to which the synchronizing signal supplied from the synchronizing signal generator 34 has been added, and it is displayed as an animated picture in the window W1 on the liquid crystal display 5 through the video board 25. This control is all effected by the CPU mother board 28 through the universal bus 27.

The above-described embodiment is a case applied to a non-mydriatic camera for eye fundus, but if in FIG. 2, the visible light cut filter 13 is eliminated and the infrared absorbing filter 22 is always inserted in the optical path, observation and phototaking will become possible by visible light and therefore, the above-described embodiment can be used as a mydriatic type eye fundus camera.

When a high resolution image pickup element having millions of pixels is used as the image pickup element 23 and an animated picture is to be displayed, the resolution of the image pickup element 23 itself exceeds the upper limit of the resolution by the frequency band of the television signal and it is impossible to make the most of the performance of the image pickup element 23. Also, when the image pickup element 23 is driven at a television signal rate and all signals are outputted, the quantity of information becomes great and the signal frequency corresponding to each pixel becomes very high and therefore, an image pickup element capable of performing a high-speed operation becomes necessary as the image pickup element 23 for effecting signal processing, and this gives rise to an inconvenience in terms of cost and electrical noise.

Accordingly, when the drive system of the image pickup element 23 is changed by the action of the image pickup element drive circuit 36 and for example, an animated picture is displayed, a system for thinning and driving pixels to a sufficient degree as a television signal, such as reading out every other pixel, is adopted whereby the amount of information of a signal outputted from the image pickup element 23 can be curtailed and signal processing necessary for the animated picture can be effected simply.

The examiner moves the operating rod 6 to thereby effect the alignment with the eye to be examined and determine a region to be phototaken while looking at the animated picture displayed on the window W1 in the liquid crystal display 5. When the region to be phototaken is set and the examiner pushes the phototaking switch 6a on the upper portion of the operating rod 6, the signal from the phototaking switch 6a is inputted to the timing generating circuit 38 for operating the various circuits of the driver board 24 at a predetermined timing, and the switch 31b is changed over by the output from the timing generating circuit 38, and the image pickup element drive circuit 37 for still pictures is driven, whereby light emitting signals are outputted to the strobe generating circuit 26.

The strobe generating circuit 26 drives the light source 14 for phototaking to thereby generate strobe light and at the same time, the infrared absorbing filter 22 is inserted into the optical path, whereby infrared light impinging on the image pickup element 23 is cut. The strobe light from the light source 14 for phototaking follows an optical path similar to that followed by the light beam for observation, and forms the image of the fundus of the eye on the image pickup element 23.

The image signal of this image of the fundus of the eye is signal-processed by the still picture signal processing circuit 32, is digitized by the A/D converter 33, and is outputted as image data onto the universal bus 27. The image pickup element drive circuit 32 for still pictures drives the image pickup element 23 so as to make all pixels thereof effective and output them, in accordance with a predetermined clock signal. Signal processing, such as the accumulation time of the image pickup element 23 and the transfer of the image signal during the phototaking of a still picture, can be carried out entirely independently of the television signal and therefore, when a highly minute image is to be phototaken by the use of an image pickup element 23 particularly having a great number of pixels, it becomes unnecessary to drive each element at a high speed, and this provides an advantage in circuit construction.

In the present embodiment, the image pickup element drive circuit 36 for animated pictures and the image pickup element drive circuit 32 for still pictures are provided for exclusive use, and these two circuits are changed over by the switches 31a and 31b, but if design is made such that the timing for driving the image pickup element drive circuits 32 and 36 and the setting of the read-out pixels are changed to thereby change over the driving of the animated picture and the still picture, it will be unnecessary to provide the image pickup element drive circuits 32 and 36 discretely from each other.

The phototaken digital image information is stored in the RAM on the CPU mother board 28 through the universal bus 27 and at the same time, is displayed on the liquid crystal display 5 by the video board 25 with the aid of software. As shown in FIG. 1, on the liquid crystal display 5, a still picture is displayed on the window W2 displayed greatly, an animated picture is displayed on the window W1 displayed small, and the ID number and name of the patient of the phototaken image are displayed on the other window W3. In this manner, character information, image information and all information about the other user interface can be displayed on the liquid crystal display 5.

Actually, these operations are performed with the video board 25 controlled by the CPU mother board 28, but if an attempt is made to display these bits of information on a television monitor, such as ordinary NTSC, the control circuit will become complicated. If an ordinary computer display such as VGA or SVGA is used as a signal form, there are 640×480 dots or more for the former and 800×600 dots or more for the latter, and this is better in terms of resolution than the television signal and thus, the display of a highly minute image is possible. Particularly, when a digitized still picture is to be displayed on a television monitor, it is again D/A-converted into a television signal and therefore, there occurs the deterioration of the image by the frequency band of the signal, but when it is to be displayed on a computer display, control is effected at the unit of dot and therefore, the computer display can display the image without diminution of the resolution of the image.

As described above, the image pickup means is driven by different drive systems for an animated picture and a still picture, and in the respective cases, the signal converting means is changed, whereby both of the animated picture and the still picture can be outputted by a signal image pickup means and also, with respect to the animated picture and the still picture, the images can be displayed at optimum speeds and resolutions.

Also, the image signal from the image pickup means is digitally converted and the digital image is displayed on the contained display for the contained computer, whereby being free from the signal band of the television signal, the phototaken image can be displayed with its resolution unchanged and also, enlarged display and reduced display as well as the display of a plurality of images become possible and the input from outside, such as the mouse and the track ball, becomes possible and therefore, operability can be improved.

Also, the animated image and still image from the image pickup means are displayed on a signal display for a computer, whereby the examiner can simply look at the same screen to thereby easily effect the alignment with the eye to be examined, the determination of the region to be phototaken, the confirmation of phototaking, diagnosis, etc.

What is claimed is:

1. An apparatus for phototaking the image of an eye to be examined comprising:

an image pickup element for picking up the image of the eye to be examined;

a first signal converting system for converting an image signal from said image pickup element into a signal for animated picture display;

a second signal converting system for converting the image signal from said image pickup element into a digital image signal; and an image pickup element drive system for driving said image pickup element for animated picture display corresponding to the converting performed by said first signal converting system and for driving said image pickup element for digital image signal display corresponding to the converting performed by said second signal converting system.

2. The apparatus according to claim 1, further having a switch member for selecting one of said first signal converting system and said second signal converting system whereby the image signal from said image pickup element is outputted to said one of said first and second signal converting systems.

3. The apparatus according to claim 2, wherein said image pickup element drive system comprises an image pickup drive circuit for an animated picture and an image pickup drive circuit for a still picture, and wherein said image pickup selects one of said pickup drive circuit for an animated picture and said pickup drive circuit for a still picture for driving said image pickup element, and selects one of said first signal converting system and said second signal converting system for use in driving said image pickup element.

4. The apparatus according to claim 1, wherein said signal for animated picture display is a television signal.

5. An apparatus for phototaking the image of an eye to be examined comprising:

an image pickup element for picking up the image of the eye to be examined;

a first signal converting system for converting an image signal from said image pickup element into a signal for animated picture display;

a second signal converting system for converting the image signal from said image pickup element into a digital image signal;

a signal display; and a control system for controlling said signal display to display images representing said signal for animated picture display and said digital image signal.

6. The apparatus according to claim 5, wherein said signal display is a display for a computer.

7. The apparatus according to claim 5, wherein said control system displays the animated picture and still picture of the eye to be examined in discrete windows on said display by said signal for animated picture display and said digital image signal.

8. An apparatus for phototaking an image comprising:

an image pickup element for picking up an image;

a first signal converting system for converting a first image signal from said image pickup element into a TV signal for animated picture display;

a second signal converting system for converting a second image signal from said image pickup element into a digital still image signal for still picture display; and an image pickup element drive system for driving said image pickup element for animated picture display in accordance with the TV signal from said first signal converting system and for driving said image pickup element for digital image signal display in accordance with the digital still image signal from said second signal converting system.

9. An apparatus for phototaking an image of an eye to be examined comprising:

an image pickup element for phototaking the eye to be examined;

display means for displaying an image based on a pickup signal of said third pickup element;

a first signal converting system for converting an image signal of said image pickup element, obtained by use of light with an infrared light component from the eye, into a signal for display of a moving picture; and a second signal converting system for converting an image signal of said image pickup element, obtained by use of light with a visible light component from the eye, into a signal for display of a digital still picture.

10. An apparatus according to claim 9, further comprising an illuminating light source for illuminating the eye with infrared light and an illuminating light source for illuminating the eye with visible light.

* * * * *

UNITED STATES PATENT AND TRADEMARK OFFICE
CERTIFICATE OF CORRECTION

PATENT NO.    : 6,158,864
DATED         : December 12, 2000
INVENTOR(S)   : Takashi Masuda, et al.

It is certified that error appears in the above-identified patent and that said Letters Patent is hereby corrected as shown below:

Title page,
Item [54], "APPARATUS FOR PHOTOTAKING THE IMAGE OF AN EYE COMPRISING SYSTEMS FOR CONVERTING AN IMAGE SIGNAL FROM AN IMAGE PICKUP ELEMENT INTO ANIMATED-PICTURE-DISPLAY AND DIGITAL-IMAGE SIGNALS" should read -- APPARATUS FOR PHOTOTAKING THE IMAGE OF AN EYE COMPRISING SYSTEMS FOR CONVERTING AN IMAGE FROM AN IMAGE SIGNAL PICKUP ELEMENT INTO ANIMATED OR MOVING PICTURE-DISPLAY AND DIGITAL IMAGE SIGNAL --.

Column 1,
Lines 15, 49, 56, and 65, "eye fundus" should read -- eye-fundus --.
Line 26, "have" should read -- has --.
Line 36, "memory" should read -- memory, --.

Column 2,
Line 45, "eye" should read -- eye- --.

Column 5,
Line 4, "eye fundus" should read -- eye-fundus --.

Signed and Sealed this

Twenty-seventh Day of November, 2001

*Attest:*

*Attesting Officer*

NICHOLAS P. GODICI
*Acting Director of the United States Patent and Trademark Office*